United States Patent
Valouev et al.

(10) Patent No.: US 11,566,284 B2
(45) Date of Patent: Jan. 31, 2023

(54) METHODS OF PREPARING DUAL-INDEXED DNA LIBRARIES FOR BISULFITE CONVERSION SEQUENCING

(71) Applicant: GRAIL, LLC, Menlo Park, CA (US)

(72) Inventors: Anton Valouev, Menlo Park, CA (US); Arash Jamshidi, Menlo Park, CA (US)

(73) Assignee: GRAIL, LLC, Menlo Park, CA (US)

( * ) Notice: Subject to any disclaimer, the term of this patent is extended or adjusted under 35 U.S.C. 154(b) by 526 days.

(21) Appl. No.: 15/674,003

(22) Filed: Aug. 10, 2017

(65) Prior Publication Data

US 2018/0044731 A1 Feb. 15, 2018

Related U.S. Application Data

(60) Provisional application No. 62/397,650, filed on Sep. 21, 2016, provisional application No. 62/373,261, filed on Aug. 10, 2016.

(51) Int. Cl.
*C12Q 1/68* (2018.01)
*C12Q 1/6874* (2018.01)
*C12Q 1/6869* (2018.01)

(52) U.S. Cl.
CPC ......... *C12Q 1/6874* (2013.01); *C12Q 1/6869* (2013.01)

(58) Field of Classification Search
CPC ............................ C12Q 1/6874; C12Q 1/6869
See application file for complete search history.

(56) References Cited

U.S. PATENT DOCUMENTS

| | | | |
|---|---|---|---|
| 814,001 A | 2/1906 | Carleton | |
| 6,773,897 B2 | 8/2004 | Herman et al. | |
| 7,229,759 B2 | 6/2007 | Olek et al. | |
| 7,534,570 B2 | 5/2009 | Berlin et al. | |
| 7,670,777 B2 | 3/2010 | Berlin et al. | |
| 7,749,702 B2 | 7/2010 | Lofton-Day et al. | |
| 7,932,027 B2 | 4/2011 | Fassbender et al. | |
| 7,943,308 B2 | 5/2011 | Lofton-Day et al. | |
| 8,062,849 B2 | 11/2011 | Sukumar et al. | |
| 8,101,359 B2 | 1/2012 | Foekens et al. | |
| 8,143,001 B2 | 3/2012 | Kurn et al. | |
| 8,163,488 B2 | 4/2012 | Lofton-Day et al. | |
| 8,241,885 B2 | 8/2012 | Bryan | |
| 8,486,634 B2 | 7/2013 | Lim et al. | |
| 8,586,310 B2 | 11/2013 | Mitra et al. | |
| 8,673,555 B2 | 3/2014 | Taylor et al. | |
| 8,753,810 B2 | 6/2014 | Tetzner et al. | |
| 8,771,939 B2 | 7/2014 | Tetzner et al. | |
| 8,822,155 B2 | 9/2014 | Sukumar et al. | |
| 8,912,129 B2 | 12/2014 | Lewin et al. | |
| 8,927,209 B2 | 1/2015 | Hamamoto et al. | |
| 8,962,246 B2 | 2/2015 | Ballhause et al. | |
| 9,017,944 B2 | 4/2015 | Foekens et al. | |
| 9,115,386 B2 | 8/2015 | Rao et al. | |
| 9,121,061 B2 | 9/2015 | Vaisvila et al. | |
| 9,121,069 B2 | 9/2015 | Lo et al. | |
| 9,181,587 B2 | 11/2015 | Day et al. | |
| 9,183,349 B2 | 11/2015 | Kupershmidt et al. | |
| 9,200,260 B2 | 12/2015 | Correa, Jr. et al. | |
| 9,267,117 B2 | 2/2016 | Guan et al. | |
| 9,290,803 B2 | 3/2016 | Laird et al. | |
| 9,290,807 B2 | 3/2016 | Booth et al. | |
| 9,292,660 B2 | 3/2016 | Von et al. | |
| 9,416,404 B2 | 8/2016 | Sukumar et al. | |
| 9,447,452 B2 | 9/2016 | Rao et al. | |
| 9,464,277 B2 | 10/2016 | Zheng et al. | |
| 9,605,306 B2 | 3/2017 | Sledziewski et al. | |
| 9,624,530 B2 | 4/2017 | Lewin et al. | |
| 9,632,093 B2 | 4/2017 | Taylor et al. | |
| 9,633,166 B2 | 4/2017 | Kupershmidt et al. | |
| 9,670,546 B2 | 6/2017 | Dietrich et al. | |
| 9,719,131 B2 | 8/2017 | Olek et al. | |
| 9,745,614 B2 | 8/2017 | Schroeder et al. | |
| 2002/0045257 A1 | 4/2002 | Feinberg et al. | |
| 2003/0009990 A1 | 1/2003 | Main et al. | |
| 2005/0196792 A1* | 9/2005 | Fodor ................. | C12Q 1/6827 435/6.12 |
| 2005/0221314 A1 | 10/2005 | Berlin et al. | |
| 2006/0194208 A1 | 8/2006 | Tetzner et al. | |
| 2007/0065824 A1 | 3/2007 | Gutig | |
| 2007/0141582 A1 | 6/2007 | Li et al. | |
| 2008/0081338 A1 | 4/2008 | Lo et al. | |
| 2008/0254470 A1 | 10/2008 | Berlin | |
| 2009/0111707 A1 | 4/2009 | Foekens et al. | |
| 2009/0280479 A1 | 11/2009 | Hoon et al. | |
| 2010/0068720 A1 | 3/2010 | Li et al. | |

(Continued)

FOREIGN PATENT DOCUMENTS

| | | | |
|---|---|---|---|
| DE | 10331107 B3 | 12/2004 | |
| EP | 1342794 B1 | 12/2005 | |

(Continued)

OTHER PUBLICATIONS

Pedersen et al. (BMC molecular biology 13.1 (2012): 12; 8 pages). (Year: 2012).*
Best, Katharine, et al. "Computational analysis of stochastic heterogeneity in PCR amplification efficiency revealed by single molecule barcoding." Scientific reports 5.1 (2015): 1-13. (Year: 2015).*
BEST 2015 supplementary materials (Year: 2015).*
EP17840272.3 Search Report dated Feb. 28, 2020.
Mirabello , et al. , "HPV16 methyl-halotypes determined by a novel next-generation sequencing method are associated with cervical precancer: HPV16 methylation and cervical precancer" , International Journal of Cancer, vol. 136, No. 4 , 2015 , E146-E153.

(Continued)

*Primary Examiner* — Sahana S Kaup

(74) *Attorney, Agent, or Firm* — Fenwick & West LLP

(57) ABSTRACT

Described herein are methods of preparing dual-indexed nucleic acid libraries for methylation profiling using bisulfite conversion sequencing. In various embodiments, the methods use a two-step indexing process to tag bisulfite-treated DNA with unique molecular identifiers (UMIs).

15 Claims, 3 Drawing Sheets

(56) References Cited

U.S. PATENT DOCUMENTS

| | | |
|---|---|---|
| 2010/0273164 A1 | 10/2010 | Church et al. |
| 2011/0039719 A1 | 2/2011 | Lofton-Day et al. |
| 2011/0171637 A1 | 7/2011 | Tetzner et al. |
| 2012/0149593 A1 | 6/2012 | Hicks et al. |
| 2013/0085681 A1 | 4/2013 | Deciu et al. |
| 2014/0080715 A1 | 3/2014 | Lo et al. |
| 2014/0179564 A1 | 6/2014 | Korlach et al. |
| 2014/0274729 A1* | 9/2014 | Kurn .................. B01J 19/0046 506/2 |
| 2014/0357497 A1 | 12/2014 | Zhang et al. |
| 2015/0011396 A1 | 1/2015 | Schroeder et al. |
| 2015/0011403 A1 | 1/2015 | Lo et al. |
| 2015/0031021 A1 | 1/2015 | Lewin et al. |
| 2015/0057183 A1 | 2/2015 | Lewin et al. |
| 2015/0099670 A1* | 4/2015 | Li ....................... C12Q 1/6855 506/26 |
| 2015/0284769 A1 | 10/2015 | Schroeder et al. |
| 2015/0299781 A1 | 10/2015 | Ost |
| 2015/0322506 A1 | 11/2015 | Vaisvila et al. |
| 2015/0322513 A1 | 11/2015 | Gromminger et al. |
| 2016/0017419 A1 | 1/2016 | Chiu et al. |
| 2016/0046981 A1 | 2/2016 | Correa, Jr. et al. |
| 2016/0138079 A1 | 5/2016 | Guan et al. |
| 2016/0168648 A1 | 6/2016 | Allawi et al. |
| 2016/0258014 A1 | 9/2016 | Booth et al. |
| 2016/0265042 A1 | 9/2016 | Schroeder et al. |
| 2016/0298183 A1 | 10/2016 | Wen et al. |
| 2016/0304964 A1 | 10/2016 | Lofton-Day et al. |
| 2016/0340740 A1 | 11/2016 | Zhang |
| 2016/0369356 A1 | 12/2016 | Liebenberg et al. |
| 2017/0067119 A1 | 3/2017 | Sledziewski et al. |
| 2017/0067120 A1 | 3/2017 | Sledziewski et al. |
| 2017/0073774 A1 | 3/2017 | Lo et al. |
| 2017/0101685 A1 | 4/2017 | Lo et al. |
| 2017/0168043 A1 | 6/2017 | Rao et al. |
| 2017/0176420 A1 | 6/2017 | Rao et al. |
| 2017/0176421 A1 | 6/2017 | Rao et al. |
| 2017/0177793 A1 | 6/2017 | Kupershmidt et al. |
| 2017/0191119 A1 | 7/2017 | Rao et al. |
| 2017/0198344 A1 | 7/2017 | Vaisvila et al. |
| 2017/0198361 A1 | 7/2017 | Taylor et al. |
| 2017/0219589 A1 | 8/2017 | Rao et al. |

FOREIGN PATENT DOCUMENTS

| | | | |
|---|---|---|---|
| EP | 2474626 A2 | 7/2012 | |
| EP | 3174996 A1 | 6/2017 | |
| WO | WO 2008/017411 A2 | 2/2008 | |
| WO | WO 2008/135512 A2 | 11/2008 | |
| WO | WO-2010085343 A1 | 7/2010 | |
| WO | WO-2011038507 A1 | 4/2011 | |
| WO | WO-2013142389 A1 * | 9/2013 | ........... C12Q 1/6806 |
| WO | WO-2014116881 A1 * | 7/2014 | ........... C12Q 1/6869 |
| WO | WO-2015103339 A1 * | 7/2015 | ....... C12Q 2525/191 |
| WO | WO-2015124955 A1 * | 8/2015 | ........... C12Q 1/6806 |
| WO | WO-2016016639 A1 | 2/2016 | |
| WO | WO-2016040602 A1 | 3/2016 | |
| WO | WO-2016063034 A1 | 4/2016 | |
| WO | WO-2016063059 A1 | 4/2016 | |
| WO | WO-2016094813 A1 | 6/2016 | |
| WO | WO-2016101258 A1 | 6/2016 | |
| WO | WO-2016127944 A1 | 8/2016 | |
| WO | WO-2016154330 A1 | 9/2016 | |
| WO | WO-2016189288 A1 | 12/2016 | |
| WO | WO-2017027835 A1 | 2/2017 | |
| WO | WO-2018031760 A1 | 2/2018 | |

OTHER PUBLICATIONS

Reuter, et al., "Simul-seq: combined DNA and RNA sequencing for whole-genome and transcriptome profiling", Nature Methods, Advance Online Publication doi:10.1038/nmeth.4028, vol. 13, issue 11, 953-958 (2016).

Sun et al., "Characterization of HPV DNA methylation of contiguouse CpG sites by bisulfite treatment and massively parallel sequencing "the FRAGMENT approach"", Frontiers in Genetics, vol. 5, art. 150 pp. 1-8 (2014).

Wittenberger, et al., "DNA methylation markers for early detection of women's cancer: promise and challenges", Epigenomics, vol. 6, No. 3, 311-327 (2014).

International Application No. PCT/US2017/046280 International Search Report and Written Opinion dated Nov. 21, 2017.

Burnham, P. et al. Single-Stranded DNA library preparation uncovers the origin and diversity of ultrashort cell-free DNA in plasma. Scientific Reports 6(27859): 1-9 (@016).

Chan, K.C. Allen, et al. Noninvasive detection of cancer-associated genome-wide hypomethylation and copy number aberrations by plasma DNA bisulfite sequences. PNAS 110(47):18761-18768 (Nov. 19, 2013).

Varley, K.E. et al. Bisulfite Patch PCR enables multiplexed sequencing of promoter methylation across cancer samples. Genome Research 20:1279-1287 (2010).

Raine, A. et al. Splinted Ligation Adapter Tagging (SPLAT), a novel library preparation method for whole genome bisulphite sequencing. Nucleic Acids Research, 110:1-15 (Nov. 28, 2016).

Bhattacharjee, B. et al., "CpG methylation of HPV 16 LCR at E2 binding site proximal to P97 is associated with cervical cancer in presence of intact E2," Virology, vol. 354, Aug. 14, 2006, pp. 280-285.

European Patent Office, Office Action, EP Patent Application No. 17840272.3, dated Jan. 13, 2022, four pages.

* cited by examiner

METHODS OF PREPARING DUAL-INDEXED DNA LIBRARIES FOR BISULFITE CONVERSION SEQUENCING

CROSS REFERENCE TO RELATED APPLICATIONS

The present application claims benefit of priority of U.S. Provisional Application Ser. No. 62/373,261 filed on Aug. 10, 2016, and U.S. Provisional Application Ser. No. 62/397,650 filed on Sep. 21, 2016, both of which are herein incorporated by reference in their entirety.

BACKGROUND OF THE INVENTION

DNA methylation plays an important role in regulating gene expression. Aberrant DNA methylation has been implicated in many disease processes, including cancer. DNA methylation profiling using bisulfite conversion sequencing is increasingly recognized as a valuable diagnostic tool for detection and diagnosis of cancer. For example, specific patterns of differentially methylated regions and/or allele specific methylations can be used as molecular markers for non-invasive diagnostics using circulating cell-free DNA. However, amplification and/or sequencing artifacts (errors) introduced during library preparation and/or sequencing can bias the results of DNA methylation analysis. There is a need for new methods of preparing a DNA library for bisulfite conversion sequencing for methylation profiling.

SUMMARY OF THE INVENTION

Disclosed herein are methods of preparing dual-indexed nucleic acid libraries for methylation profiling using bisulfite or enzymatic conversion sequencing. In various embodiments, the methods use a two-step indexing process to tag bisulfite-treated or enzymatically converted DNA (in which unmethylated cytosines are converted to uracils in the converted DNA) with unique molecular identifiers (UMIs), wherein a first UMI is added to converted DNA using a single-strand DNA (ssDNA) ligation reaction and a second UMI is added in a subsequent processing step (e.g., a double-strand ligation step). The UMIs are used to identify individual DNA molecules and reduce or substantially eliminate sequencing and/or amplification-induced artifacts (based on a consensus among reads sharing the same UMI) thereby increasing the accuracy of DNA methylation analysis.

In certain embodiments, described herein, is a method of determining a methylation profile of an individual comprising: obtaining a biological sample from the individual; converting unmethylated cytosines to uracils in nucleic acid molecules of the biological sample to produce bisulfite converted nucleic acid molecules; determining the nucleic acid sequence of the converted nucleic acid molecules; and comparing the nucleic acid sequence of the converted nucleic acid molecules to a reference nucleic acid sequence, to determine the methylation profile of the individual. In certain embodiments, the individual is a human. In certain embodiments, the biological sample comprises blood, serum, plasma, urine, cerebral spinal fluid, or lymph. In certain embodiments, converting unmethylated cytosines to uracils comprises incubation with bisulfite ion. In certain embodiments, the nucleic acid molecules are DNA. In certain embodiments, the DNA is cell-free DNA. In certain embodiments, the cell-free DNA is derived from a linear chromosome. In certain embodiments, the linear chromosome is an autosome. In certain embodiments, the method further comprises ligating a nucleic acid adapter to the converted nucleic acids. In certain embodiments, the nucleic acid adapter comprises a unique molecular identifier. In certain embodiments, the nucleic acid adapter comprises a universal priming site. In certain embodiments, the nucleic acid adapter is single stranded. In certain embodiments, the nucleic acid adapter is partially single stranded and partially double stranded. In certain embodiments, ligating the nucleic acid adapter is performed on single stranded nucleic acids. In certain embodiments, the nucleic acid adapter is attached to a solid support. In certain embodiments, the solid support is a bead. In certain embodiments, the bead is heat labile. In certain embodiments, the method further comprises performing primer extension of the converted nucleic acid molecules, unconverted nucleic acid molecules, or both. In certain embodiments, the method further comprises ligating a nucleic acid adapter to a second end of the converted nucleic acid molecules. In certain embodiments, ligating the nucleic acid adapter to a second end of the converted nucleic acid molecules creates a gap between a 5' end of the converted nucleic acid molecules and a 3' end of the third adapter most proximal to the 5' end of the converted nucleic acid molecules. In certain embodiments, the method further comprises amplifying the converted nucleic acid molecules before determining the nucleic acid sequence. In certain embodiments, the amplifying comprises polymerase chain reaction. In certain embodiments, the amplifying results in the addition of sequencing adapters to the converted nucleic acid molecules, the unconverted nucleic acid molecules, or both. In certain embodiments, determining the nucleic acid sequence comprises next-generation sequencing. In certain embodiments, determining the nucleic acid sequence comprises sequencing by synthesis, pyrosequencing, or ion semi-conductor sequencing. In certain embodiments, determining the nucleic acid sequence comprises sequencing to a depth of at least 10,000×. In certain embodiments, the methylation profile is used to screen for or diagnose an autoimmune disease. In certain embodiments, the methylation profile is used to screen for or diagnose cancer. In certain embodiments, the methylation profile is used to screen for or diagnose organ damage, organ disease, or organ failure. In certain embodiments, the methylation profile is used to screen for or diagnose transplant rejection. In certain embodiments, the method further comprises using the methylation profile in combination with any of family history, clinical data, genome sequencing data, proteomic data, or microbiome data to screen for or diagnose autoimmune disease, cancer, organ failure, or organ transplant rejection.

In certain embodiments, descried herein is a method of determining a methylation profile of an individual comprising: (a) obtaining a biological sample from the individual; (b) converting unmethylated cytosines to uracils in nucleic acid molecules of the biological sample to produce converted nucleic acid molecules; (c) ligating a nucleic acid adapter comprising a unique molecular identifier to the converted nucleic acids; (d) determining the nucleic acid sequence of the converted nucleic acid molecules; and (e) comparing the nucleic acid sequence of the converted nucleic acid molecules to a reference nucleic acid sequence, to determine the methylation profile of the individual. In certain embodiments, the biological sample comprises blood, serum, plasma, urine, cerebral spinal fluid, or lymph. In certain embodiments, the method further comprises enriching the converted nucleic acid molecules, wherein the enrichment increases the amount of more target molecules compared to non targeted. In certain embodiments, converting unmethylated cytosines to uracils comprises incubation with bisulfite ion. In certain embodiments, converting unmethylated cytosines to uracils comprises incubation with a cytidine deaminase. In certain embodiments, the nucleic acid molecules are DNA. In certain embodiments, the DNA is cell-free DNA (cfDNA). In certain embodiments, the nucleic acid adapter comprises a universal priming site. In certain embodiments, the nucleic acid adapter is partially single stranded and partially double stranded. In certain embodiments, ligating the nucleic acid adapter is performed on single stranded nucleic acids. In certain embodiments, nucleic acid adapter is attached to a solid support. In certain embodiments, the solid support is a bead. In certain embodiments, the method further comprises performing primer extension of the converted nucleic acid molecules, unconverted nucleic acid molecules, or both. In certain embodiments, the method further comprises ligating a nucleic acid adapter to a second end of the converted nucleic acid molecules. In certain embodiments, ligating the nucleic acid adapter to a second end of the converted nucleic acid molecules creates a gap between a 5' end of the converted nucleic acid molecules and a 3' end of the third adapter most proximal to the 5' end of the converted nucleic acid molecules. In certain embodiments, the method further comprises amplifying the converted nucleic acid molecules before determining the nucleic acid sequence. In certain embodiments, amplifying comprises polymerase chain reaction. In certain embodiments, the amplifying results in the addition of sequencing adapters to the converted nucleic acid molecules, the unconverted nucleic acid molecules, or both. In certain embodiments, determining the nucleic acid sequence comprises next-generation sequencing. In certain embodiments, determining the nucleic acid sequence comprises sequencing to a depth of at least 10,000×. In certain embodiments, the methylation profile is used to screen for or diagnose cancer. In certain embodiments, the methylation profile is used determine a tissue or origin of a cell-free DNA.

In certain embodiments, described herein, is a method of determining a methylation profile of an individual comprising: obtaining a biological sample from the individual that is divided into at least two aliquots; converting unmethylated cytosines to uracils in nucleic acid molecules of a first aliquot to produce a first aliquot comprising bisulfite converted nucleic acid molecules; determining the nucleic acid sequence of the converted nucleic acid molecules and the nucleic acid molecules of a second aliquot comprising unconverted nucleic acid molecules wherein the unmethylated cytosines are not converted to uracils; and comparing the nucleic acid sequence of the converted nucleic acid molecules and the unconverted nucleic acid molecules, to determine the methylation profile of the individual. In certain embodiments, the individual is a human. In certain embodiments, the biological sample comprises blood, serum, plasma, urine, cerebral spinal fluid, or lymph. In certain embodiments, converting unmethylated cytosines to uracils comprises incubation with bisulfite ion. In certain embodiments, the at least two aliquots are at least about equal. In certain embodiments, the nucleic acid molecules are DNA. In certain embodiments, the DNA is cell-free DNA. In certain embodiments, the cell-free DNA is derived from a linear chromosome. In certain embodiments, the linear chromosome is an autosome. In certain embodiments, the method further comprises ligating a nucleic acid adapter to the converted nucleic acids, the unconverted nucleic acids, or both. In certain embodiments, the nucleic acid adapter comprises a unique molecular identifier. In certain embodiments, the nucleic acid adapter comprises a universal priming site. In certain embodiments, the nucleic acid adapter is single stranded. In certain embodiments, the nucleic acid adapter is partially single stranded and partially double stranded. In certain embodiments, ligating the nucleic acid adapter is performed on single stranded nucleic acids. In certain embodiments, the nucleic acid adapter is attached to a solid support. In certain embodiments, the solid support is a bead. In certain embodiments, the bead is heat labile. In certain embodiments, the method further comprises combining the at least two aliquots before determining the nucleic acid sequence. In certain embodiments, the method further comprises performing primer extension of the converted nucleic acid molecules, unconverted nucleic acid molecules, or both. In certain embodiments, the method further comprises ligating a nucleic acid adapter to a second end of the converted nucleic acid molecules, the unconverted nucleic acid molecules, or both. In certain embodiments, ligating the nucleic acid adapter to a second end of the converted nucleic acid molecules, the unconverted nucleic acid molecules, or both creates a gap between a 5' end of the converted nucleic acid molecules, the unconverted nucleic acid molecules, or both and a 3' end of the third adapter most proximal to the 5' end of the converted nucleic acid molecules, the unconverted nucleic acid molecules, or both. In certain embodiments, the method further comprises amplifying the converted nucleic acid molecules, the unconverted nucleic acid molecules, or both before determining the nucleic acid sequence. In certain embodiments, the amplifying comprises polymerase chain reaction. In certain embodiments, the amplifying results in the addition of sequencing adapters to the converted nucleic acid molecules, the unconverted nucleic acid molecules, or both. In certain embodiments, determining the nucleic acid sequence comprises next-generation sequencing. In certain embodiments, determining the nucleic acid sequence comprises sequencing by synthesis, pyrosequencing, or ion semi-conductor sequencing. In certain embodiments, determining the nucleic acid sequence comprises sequencing to a depth of at least 10,000×. In certain embodiments, the nucleic acid sequence of the converted nucleic acid molecules and the unconverted nucleic acid molecules are compared to determine cytosines from the nucleic acid molecules of the first aliquot that were converted to uracils based upon a sequence of the nucleic acid adapter. In certain embodiments, the methylation profile is used to screen for or diagnose an autoimmune disease. In certain embodiments, the methylation profile is used to screen for or diagnose cancer. In certain embodiments, the methylation profile is used to screen for or diagnose organ damage, organ disease, or organ failure. In certain embodiments, the methylation profile is used to screen for or diagnose transplant rejection. In certain embodiments, the method further comprises using the methylation profile in combination with any of family history, clinical data, genome sequencing data, proteomic data, or microbiome data to screen for or diagnose autoimmune disease, cancer, organ failure, or organ transplant rejection.

In certain embodiments, described herein, is a method of preparing a nucleic acid library for bisulfite conversion sequencing comprising: converting unmethylated cytosines to uracils in nucleic acid molecules of a sample to produce a converted nucleic acid molecules; and ligating a first nucleic acid adapter comprising a first unique molecular identifier and a first universal priming site to a first end of the converted nucleic acid molecules, to produce tagged converted nucleic acid molecules. In certain embodiments, the nucleic acid molecules of the sample comprise DNA. In certain embodiments, the nucleic acid molecules of the sample comprise cell-free DNA. In certain embodiments, the cell-free DNA is derived from a human linear chromosome. In certain embodiments, the human linear chromosome is an autosome. In certain embodiments, the cell-free DNA is derived from blood, serum, plasma, urine, cerebral spinal fluid, or lymph. In certain embodiments, converting unmethylated cytosines to uracils comprises incubation with bisulfite. In certain embodiments, converting the unmethylated cytosines to uracils in the nucleic acid molecules of the converted nucleic acid molecules yields tagged converted nucleic acid molecules that are single stranded. In certain embodiments, the first nucleic acid adapter is single stranded. In certain embodiments, the first nucleic acid adapter is partially single stranded and partially double stranded. In certain embodiments, the method further comprises performing primer extension on the tagged converted nucleic acid molecules with a primer that binds to the universal priming site to produce double stranded, single tagged converted nucleic acid molecules. In certain embodiments, the method further comprises ligating a second nucleic acid adapter to a second end of the double stranded, single tagged converted nucleic acid molecules, wherein the second adapter comprises a second unique molecular identifier, to produce double stranded, double tagged converted nucleic acid molecules. In certain embodiments, the sequence of the second unique molecular identifier is different from the sequence of the first unique molecular identifier. In certain embodiments, ligating the second nucleic acid adapter to a second end of the double stranded, single tagged converted nucleic acid molecules creates a gap between a 5' end of the double stranded, double tagged converted nucleic acid molecules and a 3' end of the adapter most proximal to the 5' end of the double stranded, double tagged converted nucleic acid molecules. In certain embodiments, the method further comprises amplifying the double stranded, double tagged converted nucleic acid molecules. In certain embodiments, the amplifying comprises polymerase chain reaction. In certain embodiments, amplifying the double stranded, double tagged converted nucleic acid preparation results in the addition of a sequencing adapter to the first end, the second end, or both ends of the plurality of nucleic acid molecules. In certain embodiments, the method further comprises determining the nucleic acid sequence of the double stranded, double tagged converted nucleic acid molecules. In certain embodiments, determining the nucleic acid sequence comprises sequencing the double stranded, double tagged converted nucleic acid preparation using a next-generation sequencing method. In certain embodiments, determining the next-generation sequencing method comprises sequencing by synthesis, pyrosequencing, or ion semi-conductor sequencing. In certain embodiments, the double stranded, double tagged converted nucleic acid molecules are sequenced to a depth of at least 10,000×. In certain embodiments, sequences containing the same unique molecular identifier are grouped together for analysis. In certain embodiments, the sequence is compared to a reference sequence or a sequence derived from nucleic acid molecules not treated with ion. In certain embodiments, the first nucleic adapter is immobilized on a solid support. In certain embodiments, the solid support is a bead. In certain embodiments, the bead is heat labile. In certain embodiments, the bead is compartmentalized in a liquid droplet. In certain embodiments, the method is for use in diagnosing or screening a human individual for a disease or disorder. In certain embodiments, the disease or disorder is an autoimmune disease. In certain embodiments, the disease or disorder is screening cancer. In certain embodiments, the disease or disorder is organ damage, organ disease, or organ failure. In certain embodiments, the disease or disorder is transplant rejection.

In certain embodiments, described herein, is a method of determining a methylation profile in an individual comprising: (a) converting unmethylated cytosines to uracils in nucleic acid molecules to produce single stranded converted nucleic acid molecules; (b) ligating a single-stranded first nucleic acid adapter comprising a first common barcode sequence to a first end of the converted nucleic acid molecules, to produce tagged converted nucleic acid strands; (c) performing primer extension to form a second DNA strand duplexed with the tagged converted nucleic acid strands; (d) ligating a double stranded second nucleic acid adapter comprising a second common barcode sequence and a primer region to the duplexed DNA of step (c), to produce tagged duplex DNA molecules; (e) amplifying the second strand of the tagged duplex DNA molecules to form amplified nucleic acid molecules; (f) determining the sequence of amplified nucleic acid molecules; and (g) identifying methylation sites by comparing the sequences of the amplified nucleic acid molecules to a reference genome. In certain embodiments, the first, the second, or both nucleic acid adapters further comprise a unique molecular identifier. In certain embodiments, determining the sequence of the amplified nucleic acid molecules comprises sequencing the amplified nucleic acid molecules to produce sequence reads, and collapsing the sequence reads based on the unique molecular identifier to form a consensus sequence. In certain embodiments, ligating the second nucleic acid adapter creates a gap between a 5' end of the tagged converted nucleic acid strands and a 3' end of the adapter most proximal to the 5' end of the tagged converted nucleic acid strands in the tagged duplex DNA molecules. In certain embodiments, the second nucleic acid adapter comprises a 3'-dideoxynucleotide on one strand.

In certain embodiments, described herein is a method of determining a methylation profile in an individual comprising: (a) converting unmethylated cytosines to uracils in nucleic acid molecules to produce single stranded converted nucleic acid molecules; (b) adapter tagging a first end of the converted nucleic acid molecules a first common barcode sequence, to produce tagged converted nucleic acid strands; (c) generating a second DNA strand duplexed with the tagged converted nucleic acid strands; (d) attaching an at least partially double stranded nucleic acid adapter comprising a second common barcode sequence and a primer region to the duplexed DNA of step (c) to produce tagged duplex DNA molecules; (e) amplifying the second strand of the tagged duplex DNA molecules to form amplified nucleic acid molecules; (f) determining the sequence of amplified nucleic acid molecules; and (g) identifying methylation sites by comparing the sequences of the amplified nucleic acid molecules to a reference genome. In certain embodiments, tagging a first end of the converted nucleic acid molecules comprises ligating a single stranded nucleic acid adapter comprising the first common barcode sequence. In certain embodiments, the second DNA strand comprises primer extension. In certain embodiments, the single stranded nucleic acid adapter, the double stranded nucleic acid adapter, or both nucleic acid adapters further comprise a unique molecular identifier. In certain embodiments, determining the sequence of the amplified nucleic acid molecules comprises sequencing the amplified nucleic acid molecules to produce sequence reads, and collapsing the sequence reads based on the unique molecular identifier to form a consensus sequence. In certain embodiments, ligating the second nucleic acid adapter creates a gap between a 5' end of the tagged converted nucleic acid strands and a 3' end of the adapter most proximal to the 5' end of the tagged converted nucleic acid strands in the tagged duplex DNA molecules. In certain embodiments, the second nucleic acid adapter comprises a 3'-dideoxynucleotide on one strand. In certain embodiments, converting unmethylated cytosines to uracils comprises incubation with bisulfite ion. In certain embodiments, converting unmethylated cytosines to uracils comprises incubation with a cytidine deaminase. In certain embodiments, the method further comprises enriching the converted nucleic acid molecules for one or more target molecules.

In certain embodiments, described herein, is a method of screening an individual for cancer or an increased risk of developing cancer comprising: converting unmethylated cytosines to uracils in nucleic acid molecules of a nucleic acid containing sample to produce single stranded converted nucleic acid molecules; ligating a single-stranded first nucleic acid adapter comprising a first common barcode sequence to a first end of the converted nucleic acid molecules, to produce tagged converted nucleic acid strands; performing primer extension to form a second DNA strand duplexed with the tagged converted nucleic acid strands; ligating a double stranded second nucleic acid adapter comprising a second common barcode sequence and a primer region to the duplexed DNA of step (c), to produce tagged duplex DNA molecules; amplifying the second strand of the tagged duplex DNA molecules to form amplified nucleic acid molecules determining the sequence of amplified nucleic acid molecules; identifying methylation sites by comparing the sequence of the amplified nucleic acid molecules to a reference genome to determine a methylation profile; and comparing the methylation profile to methylation profiles associated with cancer to identify if the individual has cancer or is at risk for developing cancer.

In certain embodiments, described herein, are kits comprising a bisulfite reagent; a nucleic acid adapter comprising a sample ID sequence and a universal primer binding site; and a universal primer. In certain embodiments, the nucleic acid adapter further comprises a unique molecular identifier sequence. In certain embodiments, the kit comprises a plurality of nucleic acid adapters each comprising a different unique molecular identifier sequence. In certain embodiments, the kit further comprises a nucleic acid adapter comprising a second different sample ID sequence.

DETAILED DESCRIPTION OF THE INVENTION

Figure 1:
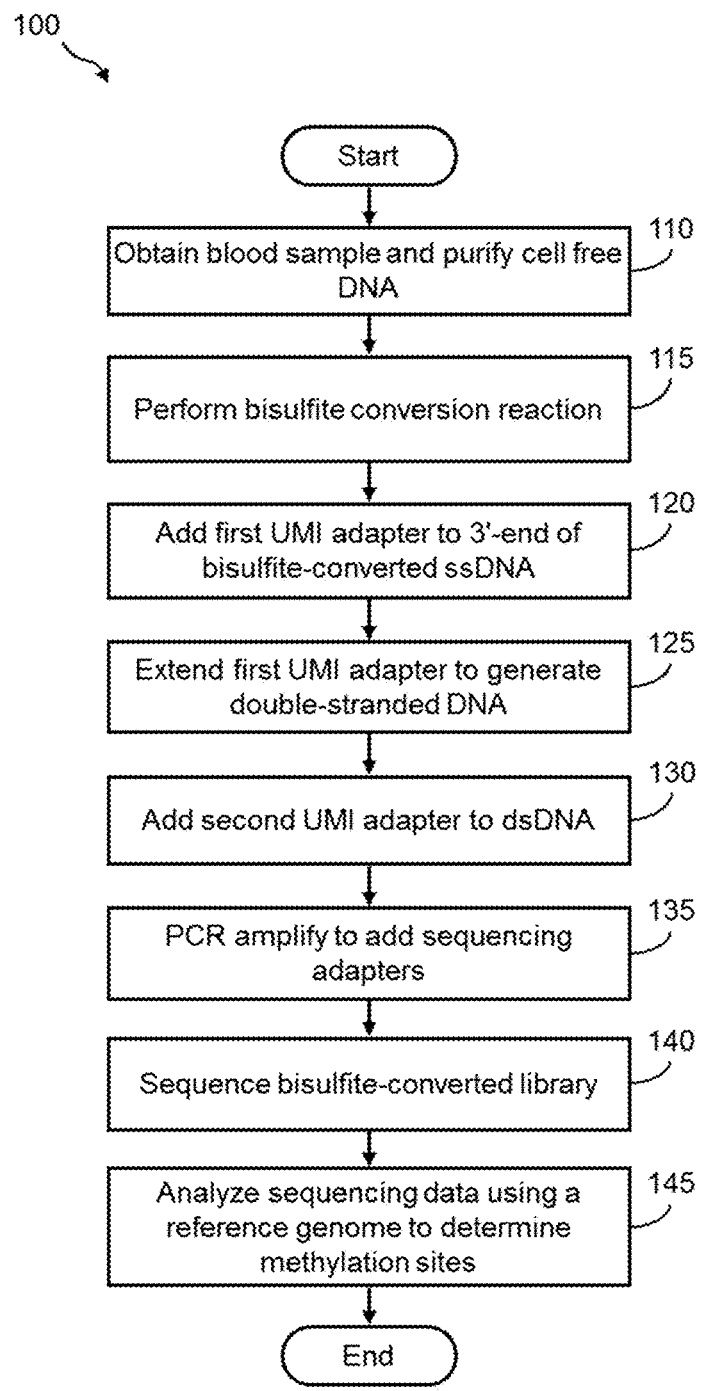
FIG. 1 illustrates a flow diagram of an example of a method of preparing a cfDNA library for bisulfite conversion sequencing.

Disclosed herein are methods of preparing dual-indexed nucleic acid libraries for methylation profiling using bisulfite conversion sequencing (in which unmethylated cytosines of the nucleic acids are converted to uracils in the converted nucleic acids). In various embodiments, the methods use a two-step indexing process to tag bisulfite-treated or enzymatically converted DNA with unique molecular identifiers (UMIs), wherein a first UMI is added to converted DNA using a single-strand DNA (ssDNA) ligation reaction and a second UMI is added in a subsequent processing step (e.g., a double-strand ligation step). The UMIs are used to identify individual DNA molecules and reduce or substantially eliminate sequencing and/or amplification-induced artifacts (based on a consensus among reads sharing the same UMI) thereby increasing the accuracy of DNA methylation analysis.

The UMIs of the present disclosure can serve many functions. The UMI can be used to identify DNA sequences originating from a common source such as a sample type, tissue, patient, or individual. The UMIs can be used to discriminate between a sample treated with bisulfite and a sample that has not been treated with bisulfite. The UMIs can include universal priming sites that allow amplification of nucleic acids that have been tagged by a UMI. The UMIs can comprise a unique (e.g., random or degenerate) nucleic acid sequence which can be used to distinguish between nucleic acid fragments in a sample. UMIs can be used to reduce amplification bias, which is the asymmetric amplification of different targets due to differences in nucleic acid composition (e.g., high GC content). The UMIs can be used to discriminate between nucleic acid mutations that arise during amplification, and mutations that were induced by bisulfite or enzymatic conversion of unmethylated cytosines to uracil.

The UMIs can be present in a multi-functional nucleic acid UMI adapter, which adapter can comprise both a sample ID and a universal priming site; a sample ID, a universal priming site, and a unique nucleic acid sequence (e.g., a random nucleic acid sequence); or a sample ID and a unique nucleic acid sequence. The sample ID portion can be any suitable length from 4 to 18, from 5 to 18, from 6 to 18, or from 7 to 18 nucleotides. The sample ID tags can be of length sufficient to identify at least 64, at least 256, at least 1024, at least 4096, at least 16,384 or more samples. The unique nucleic acid sequence portion of a UMI adapter can be greater than 5, 6, 7, 8, 9, 10, 11, 12, 13, 14, 15, 16, 17, or 18 nucleotides. The UMI adapters can comprise a defined set of unique nucleic acid sequences.

The UMIs of the present disclosure are provided in the form of nucleic acid adapters that allow the UMIs to be appended to a nucleic acid molecule using a ligation reaction. The ligation reaction can be a blunt-end ligation. The adapters can be single stranded for ligation to a single stranded nucleic acid molecule. The adapters can be double stranded for ligation to a double stranded nucleic acid molecule. In a certain embodiment a double stranded adapter can have an overhang that allows for a gap between a 3' end of the adapter and the 5' end of the nucleic acid molecule. Alternatively, the double stranded adapter comprises a dideoxy nucleotide at the 3' end of the adapter as shown in 240 of FIG. 2. In one embodiment, the methods of the invention are used for methylation profiling of cell-free DNA (cfDNA) isolated from a biological sample for detection, diagnosis or screening for a disease or disorder. The biological sample can be any of blood, plasma, serum, cerebral spinal fluid, interstitial fluid from a biopsy, urine, feces, semen, mucus (e.g., oral or vaginal), sweat, or flash-frozen paraffin embedded (FFPE) tissue samples. In certain embodiments, the biological sample is blood, plasma, or serum. The cellular source of the cfDNA can be either nuclear (chromosomal), mitochondrial or both. In certain embodiments, the cellular source of the cfDNA can be from a tissue such as the liver, kidney, pancreas, colon, stomach, esophagus, skin, lungs, ovaries, breast, uterus, prostate, testicles, peripheral blood mononuclear cells, lymphocytes, T cell, B cells, or plasma cells.

FIG. 1 illustrates a flow diagram of an example of a method 100 of preparing a cfDNA library for bisulfite conversion sequencing using adapters containing UMIs. Method 100 includes, but is not limited to, the following steps. In a step 110, a blood sample is obtained and circulating cfDNA is isolated from the plasma fraction. In a step 115, a bisulfite conversion reaction is performed on the purified cfDNA. For example, sodium bisulfite treatment converts unmethylated cytosine into uracil, which is replaced by thymine after PCR amplification, while the conversion of methylated cytosine (5-methylcytosine) occurs at a much slower rate, and therefore most methylated cytosines remain unchanged.

The conversion reaction can be performed using a standard protocol, or a commercially available kit. An exemplar protocol involves starting with isolated DNA, and denaturing the DNA with NaOH at a final concentration of about 0.3. After the DNA is denatured it can be treated with sodium bisulfite or sodium metabisulfite at final concentration of about 2M (pH between about 5 and 6) at 55° C. for 4-16 hours. This step covalently modifies unmethylated cytosines with a sulfite. After conversion the DNA is desalted followed by desulfonation by incubating the DNA at alkaline pH and room temperature, resulting in deamination—and conversion to uracil. In one example a commercial kit such as the EZ DNA Methylation—Gold, EZ DNA Methylation—Direct or an EZ DNA Methylation—Lightning kit (available from Zymo Research Corp (Irvine, Calif.)) is used for the bisulfite conversion.

Also contemplated by this disclosure is the conversion of methylated cytosines to uracils by a method not utilizing bisulfite ion. Cytidine deaminase enzyme catalyzes the irreversible hydrolytic deamination of cytidine and deoxycytidine to uridine and deoxyuridine respectively. In some embodiments, the conversion of unmethylated cytosines to uracils is accomplished via an enzymatic reaction. In some embodiments, nucleic acid molecules are incubated with cytidine deaminase. In some embodiments, the cytidine deaminase includes activation induced cytidine deaminase (AID) and apolipoprotein B mRNA editing enzymes, catalytic polypeptide-like (APOBEC). In some embodiments, the APOBEC enzyme is selected from the human APOBEC family consisting of: APOBEC-1 (Apo1), APOBEC-2 (Apo2), AID, APOBEC-3A, -3B, -3C, -3DE, -3F, -3G, -3H and APOBEC-4 (Apo4). In some embodiments, the enzyme is a variant of APOBEC (US20130244237). In some embodiments, the conversion uses a commercially available kit. In one example, a kit such as APOBEC-Seq (NEBiolabs; US20130244237) is used.

The converted nucleotides can be enriched for specific targets of interest. In certain embodiments, a converted target nucleic acid is enriched by at least 5-fold, 10-fold, 50-fold, or 100-fold compared to the unenriched target. Enrichment can be employed for 1 or more targets. In certain embodiments, at least 2, 3, 4, 5, 6, 7, 8, 9, 10 or more targets can be enriched simultaneously. Enrichment can be employed through an amplification reaction or by binding to specific bait nucleic acids that bind specific enrichment targets. Bait nucleic acids can be immobilized on a solid support such as a column or substantially flat surface. Bait nucleic acids can also be immobilized on beads or made of a magnetic material, agarose, sepharose, or some other bulky material that allows for recovery by a magnet, centrifugation, or precipitation.

Still referring to FIG. 1, in a step 120, a first UMI adapter is added to the 3'-OH ends of the bisulfite-converted ssDNA. For example, a first UMI adapter is added to the 3'-OH end of a bisulfite-converted ssDNA molecule using a ssDNA ligation reaction. A first UMI adapter includes, for example, a UMI sequence and a universal primer sequence (e.g., an SBS primer sequence). In one example, Swift Biosciences' Adaptase™ technology is used in a ssDNA ligation reaction, wherein a 3' end G-tail is added to the ssDNA template and an "adaptase" is then used to add a partially double-stranded adapter that includes a 3'-end overhang onto the template molecule. A polishing step is then used to fill in the bases and repair the nick to attach the adapter. In another example, the ssDNA ligation reaction uses CircLigase II (Epicentre) to ligate a first UMI adapter to the 3'-OH end of a bisulfite-converted ssDNA molecule, wherein the 5'-end of the UMI adapter is phosphorylated and the bisulfite-converted ssDNA has been dephosphorylated (i.e., the 3' end has a hydroxyl group). In another example, the ssDNA ligation reaction uses Thermostable 5' AppDNA/RNA ligase (available from New England BioLabs (Ipswich, Mass.)) to ligate a first UMI adapter to the 3'-OH end of a bisulfite-converted ssDNA molecule. In this example, the first UMI adapter is adenylated at the 5'-end and blocked at the 3'-end. In yet another example, the ssDNA ligation reaction uses a T4 RNA ligase (available from New England BioLabs) to ligate a first UMI adapter to the 3'-OH end of a bisulfite-converted ssDNA molecule. In a step 125, second strand DNA is synthesized in an extension reaction. For example, an extension primer that includes a primer sequence that is complementary to the universal primer sequence in the first UMI adapter is used in a primer extension reaction to form a double stranded complex. The extension reaction uses, for example, an enzyme that is able to read through uracil residues in the bisulfite-converted template strand. In a step 130, a second UMI adapter is added to the double-stranded bisulfite-converted DNA complex. For example, a second UMI adapter is a double stranded adapter that includes a UMI sequence and universal primer sequence (e.g., an SBS primer sequence), wherein one strand includes a 5'-phosphate and the other strand includes a 3'-dideoxy nucleotide (i.e., the 3'-end is blocked). The second UMI adapter is ligated to the double-stranded bisulfite-converted DNA complex using, for example, T4 DNA ligase in a blunt-end ligation reaction.

In a step 135, the double-stranded bisulfite-converted DNA is amplified to add sequencing adapters. For example, PCR amplification using a forward primer that includes a P5 sequence and a reverse primer that includes a P7 sequence is used to add P5 and P7 sequences to the bisulfite-converted DNA. In a step 140, the bisulfite-converted library is sequenced. In a step 145, the sequencing data is analyzed to determine methylation sites and patterns. In one example, the methylation sites are determined by comparing the sequence data to a reference genome. Comparison of sequence information between the reference genome and bisulfite-treated DNA can provide information about methylation patterns (e.g., cell/tissue-specific methylation, differential hypomethylation and/or hypermethylation, allele-specific methylation, etc.) that can be used, for example, to infer the tissue of origin of the cfDNA or identify DNA molecules originating from tumor cells.

Figure 2:
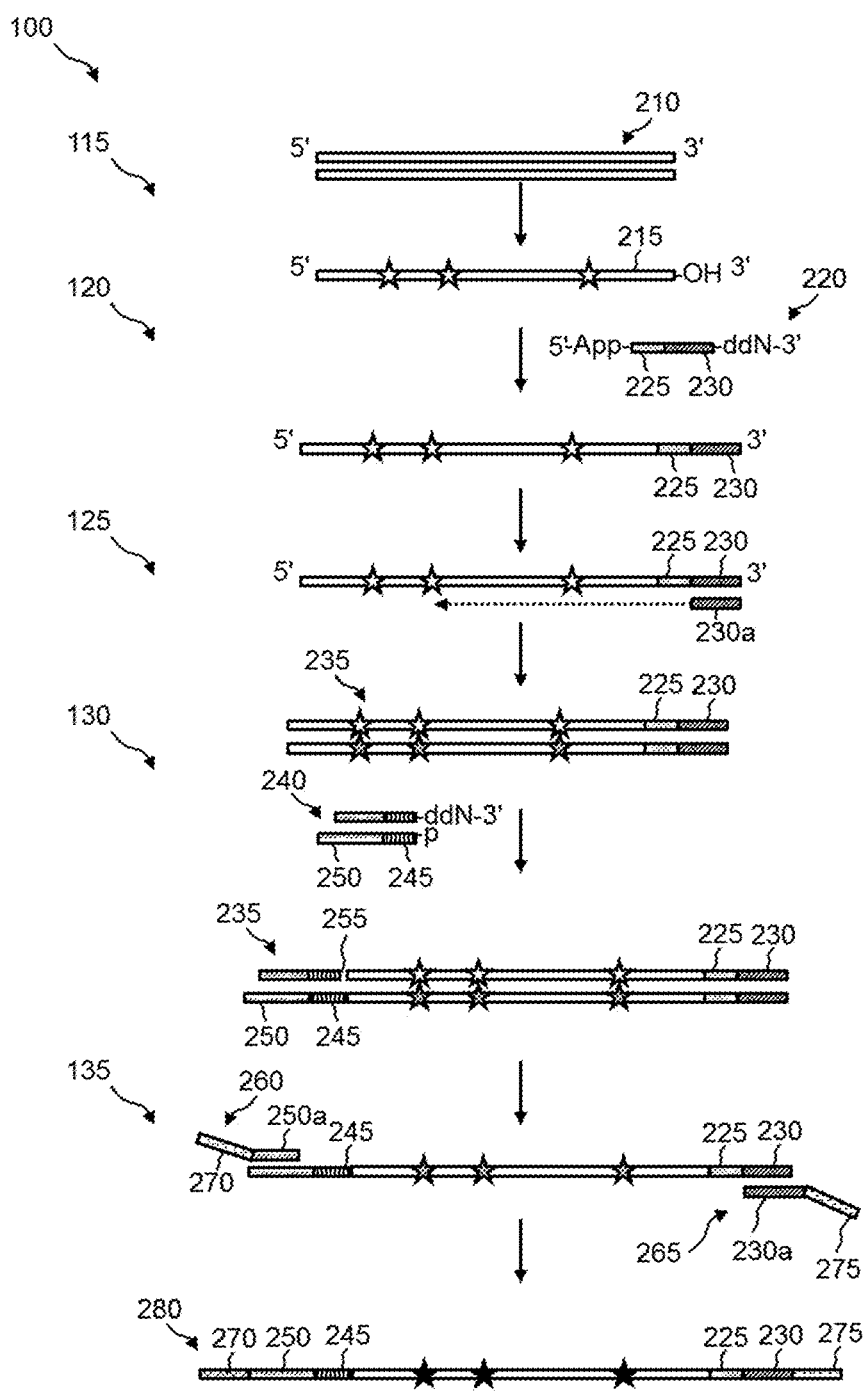
FIG. 2 shows graphically the steps of the method of FIG. 1.

FIG. 2 shows a graphical representation the steps of method 100 of FIG. 1. Namely, in step 110 (not shown in FIG. 2), a blood sample is obtained and circulating cell-free DNA is isolated from the plasma fraction. In step 115, a bisulfite conversion reaction is performed on a double-stranded DNA molecule 210 to form a bisulfite-converted single-stranded DNA molecule 215. Sodium bisulfite treatment converts an unmethylated cytosine in DNA molecule 210 into uracil (indicated by stars). In one example, an EZ DNA Methylation—Gold or an EZ DNA Methylation—Lightning kit (available from Zymo Research Corp) is used for bisulfite conversion. In an alternative step 115, the conversion of unmethylated cytosines to uracils is accomplished via an enzymatic reaction such as via incubation with cytidine deaminase. In step 120, a first UMI adapter 220 that is adenylated at the 5'-end and blocked at the 3'-end is ligated to the 3'-OH ends of bisulfite-converted or enzymatically converted ssDNA molecule 215. In this example, the ssDNA ligation reaction uses Thermostable 5' DNA/RNA ligase (not shown) to ligate first UMI adapter 220 to the 3'-OH end of bisulfite-converted ssDNA molecule 215. In step 125, second strand DNA is synthesized in an extension reaction. For example, an extension primer 230a that is complementary to the SBS primer region 230 in first UMI adapter 220 is used in a primer extension reaction to form a double stranded complex 235. The extension reaction uses, for example, an enzyme that is able to read through uracil residues (indicated by white stars) in the bisulfite-converted template strand converting the uracil to adenine (indicated by gray stars). In step 130, a second UMI adapter 240 is ligated to bisulfite-converted DNA complex 235. Second UMI adapter 240 is a double-stranded molecule that includes a second UMI region (e.g., a specific barcode sequence) and an SBS primer region 250, wherein one strand (the 3' to 5'strand, i.e., the "bottom" strand) of second UMI adapter 240 includes a 5'-phosphate and the other strand (the 5' to 3' strand, i.e., the "top" strand) includes a 3'-dideoxy nucleotide (i.e., the 3'-end is blocked). Second UMI adapter 240 is ligated to bisulfite-converted DNA complex 235 using, for example, T4 DNA ligase in a blunt-end ligation reaction. Because second UMI adapter 240 is blocked at the 3'-end, a gap 255 is created. In step 135, bisulfite-converted DNA complex 235 is amplified to add sequencing adapters. For example, an amplification reaction is performed using a forward primer 260 and a reverse primer 265. Forward primer 260 includes an SBS primer region 250a that is complementary to SBS primer region 250 and a P5 region 270. Reverse primer 265 includes an SBS region 230a that is complementary to SBS primer region 230 and a P7 region 275. Because of gap 255 in bisulfite-converted DNA complex 235, the "top" strand is not amplified during the PCR amplification step. A library amplicon 280 now includes P5 region 270, SBS primer region 250, second UMI 245, first UMI 225, SBS primer region 230, and P7 region 275. In step 140 (not shown in FIG. 2), the bisulfite-converted amplicon library is sequenced. In step 145 (not shown in FIG. 2), the sequencing data is analyzed to determine methylation sites. In one example, the methylation sites are determined by comparing the sequence data to a reference genome. Comparison of sequence information between the reference genome and bisulfite-treated DNA can provide information about methylation patterns (e.g., cell/tissue-specific methylation, differential hypomethylation and/or hypermethylation, allele-specific methylation, etc.) that can be used, for example, to infer the tissue of origin of the cfDNA or determine which molecules originate from tumor cells.

In another example (not shown), the second UMI adapter 240 is a Y-adapter, wherein the UMI sequence is included in the single-stranded portion of the Y-adapter. In this example, each strand of bisulfite-converted DNA complex 235 is labeled with a different UMI sequence and can be subsequently distinguished.

In another embodiment, methylation sites and patterns can be identified using a (+) bisulfite-converted library and a (−) bisulfite library prepared in parallel from aliquots of a single sample. The sample can be divided into one or more aliquots. In certain embodiments, the sample can be divided into 1, 2, 3, 4, 5, 6, 7, 8, 9, 10 or more aliquots. These aliquots can also be divided into replicates in certain cases duplicate, triplicate, or quadruplicate. For example, a (+) bisulfite-converted library is prepared using a first aliquot of a cfDNA sample according to method 100 of FIG. 1 using a plurality of first UMI adapters that include a UMI sequence, a universal (i.e., common) first barcode sequence, and a first universal primer sequence (e.g., a SBS primer sequence). The first universal barcode sequence is used to identify the library as a (+) bisulfite-converted library and the UMI sequences are used to identify individual DNA molecules. A second aliquot of the cfDNA is denatured a (−) bisulfite library is prepared according to steps 120 through 130 of method 100 of FIG. 1 using a plurality of second UMI adapters that include a UMI sequence, a second universal (i.e., common) barcode sequence, and a universal primer sequence (e.g., a second SBS primer sequence). The second universal barcode sequence is used to identify the library as a (−) bisulfite library and the UMI sequences in the second UMI adapter are used to identify individual DNA molecules. The (+) bisulfite-converted and the (−) bisulfite libraries are pooled and amplified to add sequencing adapters. Comparison of sequencing data from the (+) bisulfite-converted library and the (−) bisulfite libraries prepared from a single sample in parallel are used to identify methylation sites and patterns.

Figure 3:
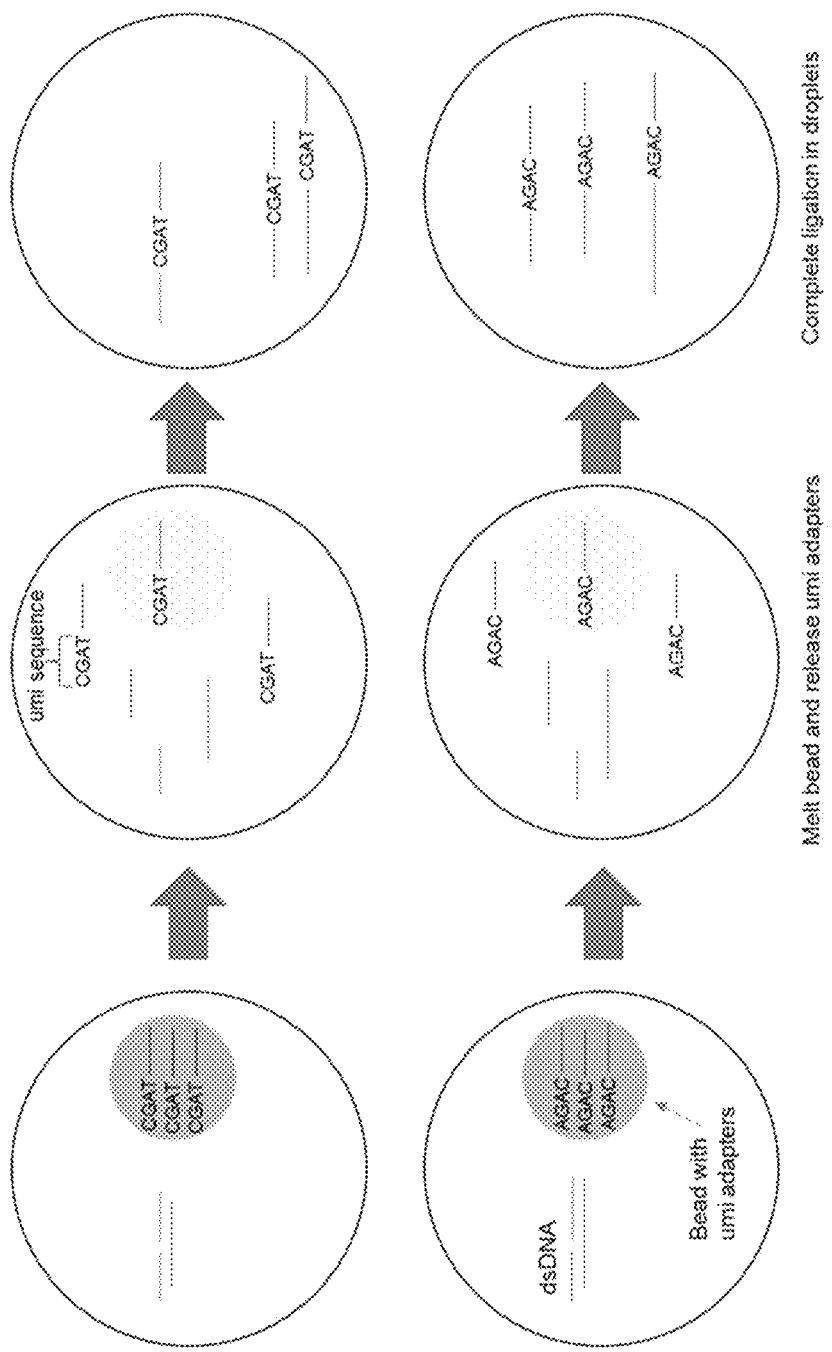
FIG. 3 shows a schematic for labeling ssDNA with a UMI sequence.

In another embodiment of the disclosure the methods solve existing problems plaguing sequencing of bisulfite treated libraries. One of the challenges with ssDNA library preparation is losing the duplex information, which means after melting the dsDNA, the top and bottom strand fragments will have different UMI sequences. Thus, in a certain embodiment, the reaction is compartmentalized in droplets or other form, such as beads, and each droplet comprises the same UMI-adapter. Thus all fragments can receive the same UMI adapter. This is shown in FIG. 3. Also, the UMI ssDNA library method is applicable to various library types such as methylation, whole-genome sequencing, and targeted deep sequencing. In a certain embodiment, the UMI adapters are bound to beads that are contained in droplets. The beads can be made of a heat labile substance such that they can be melted to release the adapter ligated nucleic acids, allowing other steps to be performed in the droplets. The material can be labile at a temperature between 60° C. and 95° C.

In certain embodiments, the nucleic acids that have been subjected to bisulfite conversion or enzymatic conversion of unmethylated cytosines to uracils have their nucleic acid sequences determined. This sequence determination is for the purpose of determining one or more cytosines that were methylated in the nucleic acids of the biological sample. In certain embodiments, a methylation profile is determined. A methylation profile is the methylation status of a plurality of cytosines in the nucleic acids of a sample. For example, a methylation status is determined for 2, 3, 4, 5, 6, 7, 8, 9, 10, 50, 100, 500, 1000 or more distinct cytosines. A methylation profile can comprise the methylation status of cytosines associated with: entire genomic regions that encompass one or more genes, promoters or enhancer elements, genes that are normally maternally or paternally imprinted, CpG islands, or CpG shores.

Sequence determination can encompass sequencing stretches of contiguous nucleic acids that are 10, 20, 30, 40, 50, 100, 150, or 300 bases in length or more. Sequence determination can also encompass the determination of distinct polymorphic markers such as single-nucleotide polymorphisms (SNPs), insertion/deletion mutations (indels), variable number tandem repeats (VNTRs), microsatellites, or minisatellites. Other disease associated genetic changes can be measured as well, such as copy number variation. The sequence can be determined using any sequencing method such as Sanger sequencing. Sequences can also be determined using a multiplex assay such as array or bead based hybridization, site specific or allele specific PCR. These methods allow the determination of 100; 1000; or 10,000 different markers simultaneously.

In a certain aspect, sequences are determined using a next-generation sequencing technology. The next generation sequencing technology can be pyrosequencing, sequencing by synthesis, or ion semiconductor sequencing. These methods are capable of sequencing at least 250 megabases per machine run. Resulting in at least 10 million discrete reads of 25 nucleotides in length or more per machine run. The sequencing reads can be paired-end reads. Combined with the methods of this disclosure this allows for sequencing at a sequencing depth of at least 10,000×, 20,000×, 30,000×, or 40,000× or more. In certain embodiments, the sequencing depth is between 10,000× and 100,000×; 20,000× and 80,000×; 30,000× and 70,000×; or 40,000× and 60,000×.

The sequencing data can be analyzed in a number of ways. The addition of UMI adapters advantageously decreases the probability of error during methylation analysis. By using UMI adapters it possible to differentiate between differences in base composition that arise from natural polymorphism, amplification error, or bisulfite conversion. Sequences that have C>T could arise by many mechanisms, for example, this C to T change could be a result of a natural polymorphism that was inherited by the individual; this could be the result of a mutation introduced during amplification; or this could be an indication that the cytosine was methylated in the original starting material. For example, if each sequence comprises two different UMI sequences one that signifies whether the sequence arises from a nucleic acid that has been subjected to bisulfite conversion or not, and one that signifies a parent nucleic acid (prior to amplification), then it is possible to analyze the sequence for changes in base composition that arise from the amplification or from conversion reaction. If the C>T is primarily present in sequences of nucleic acids that have been treated with bisulfite, but absent from sequences of nucleic acids not treated by bisulfite, then this substitution is likely a result of the deamination of an unmethylated cytosine. Sequences can also be aligned to a reference genome or reference sample.

Certain tissues possess tissue specific methylation patterns. Thus, methylation analysis can be used to trace cfDNA to a tissue of origin. The tissue could be a tissue or specific cell-type such as the heart, liver, kidney, pancreas, colon, stomach, esophagus, skin, lungs, ovaries, breast, uterus, prostate, testicles, peripheral blood mononuclear cells, lymphocytes, T cell, B cells, or plasma cells.

The methods of this disclosure are useful for diagnosis or screening of organ transplant or organ failure. They can be used to screen for heart, lung, kidney, liver, or pancreatic rejection after transplant from a donor. Increasing levels of DNA derived from a particular organ after transplant is indicative of organ failure or rejection. These methods can be performed on samples taken before and after receipt of an organ transplant. In certain embodiments, the methods can be used for surveillance post transplant. For example, these methods can be performed on samples taken longitudinally from a single transplant recipient at defined intervals. These methods are useful regardless of the gender, or genetic relationship of the donor to the recipient.

Alternatively, the methods of the disclosure are useful for diagnosis or screening for cancer. In certain embodiments, the caner is liver cancer, hepatocellular carcinoma, melanoma, pancreatic cancer, lung cancer, kidney cancer, stomach cancer, esophageal cancer, colon cancer, breast cancer, ovarian cancer, cervical cancer, testicular cancer, prostate cancer, lymphoma, B cell lymphoma, diffuse large B-cell lymphoma, follicular lymphoma, mantle cell lymphoma, small lymphocytic lymphoma, splenic marginal zone B-cell lymphoma, extranodal marginal zone B-cell lymphoma of mucosa-associated lymphoid tissue, nodal marginal zone B-cell lymphoma, lymphoplasmacytic lymphoma, primary effusion lymphoma, Burkitt lymphoma/Burkitt cell leukemia, T cell lymphoma, anaplastic large cell lymphoma (primary cutaneous type), anaplastic large cell lymphoma, (systemic type), peripheral T-cell lymphoma, angioimmunoblastic T-cell lymphoma, adult T-cell lymphoma/leukemia (human T-cell lymphotropic virus type I positive), extranodal NK/T-cell lymphoma (nasal type), enteropathy-associated T-cell lymphoma, gamma/delta hepatosplenic T-cell lymphoma, subcutaneous panniculitis-like T-cell lymphoma, multiple myeloma, mycosis fungoides. The methods of this disclosure are also useful for diagnosing or screening diseases associated with organ damage such as organ failure or autoimmune diseases, such as multiple sclerosis, type I diabetes, lupus, or rheumatoid arthritis.

In addition to diagnosis and screening for cancer, these methods are useful to gauge response to treatment. For example, these methods can be performed on samples taken at defined intervals longitudinally from a single patient receiving chemotherapy, radiation therapy, or immunotherapy. In a certain embodiment these method are useful for determining failure of a particular treatment, or relapse after successful treatment. The methods of this disclosure are useful in combination with other analyses. Methylation analysis can be combined with other analysis of cfDNA. For example, a methylation profile could be combined with quantitation of a particular cfDNA, such as a SNP or gene promoter to determine an increase relative to a threshold value or relative to a sample taken at a previous time. Methylation analysis can be combined with family history, genomic profiling, metabolic profiling, and other clinically useful tests such as biopsy, PET scan, or MRI.

While preferred embodiments of the present invention have been shown and described herein, it will be understood by those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of determining a methylation profile of an individual comprising:
   a) obtaining a biological sample from the individual;
   b) converting an unmethylated cytosine to a uracil in a nucleic acid molecule of the biological sample, thereby producing a converted nucleic acid molecule, wherein the converted nucleic acid molecule is single stranded and has a converted nucleic acid sequence;

c) ligating, with a ligase, a single stranded nucleic acid adapter comprising a unique molecular identifier to the converted nucleic acid molecule, thereby producing a single stranded adapter ligated product comprising the converted nucleic acid molecule;

d) annealing a primer to the single stranded nucleic acid adapter in the single stranded adapter ligated product and extending the primer to form a double stranded complex comprising the single stranded adapter ligated product and an extension product;

e) ligating an at least partially double-stranded nucleic acid adapter to a 3' end of the extension product, wherein the ligating the at least partially double-stranded nucleic acid adapter to the 3' end of the extension product creates a gap between a 5' end of the converted nucleic acid molecule and a 3' end of one strand of the at least partially double-stranded adapter that is not ligated to the extension product;

f) amplifying the double stranded complex comprising the single stranded adapter ligated product, the extension product, and the at least partially double stranded nucleic acid adapter that is ligated to the 3' end of the extension product, wherein the strand of the double stranded complex comprising the gap is not amplified during the amplifying step;

g) determining the converted nucleic acid sequence of the converted nucleic acid molecule of the single stranded adapter ligated product or amplification products thereof; and h) comparing the converted nucleic acid sequence to a reference nucleic acid sequence to determine the methylation profile of the individual.

2. The method of claim 1, wherein the biological sample comprises blood, serum, plasma, urine, cerebral spinal fluid, or lymph.

3. The method of claim 1, further comprising enriching the converted nucleic acid molecule.

4. The method of claim 1, wherein the converting an unmethylated cytosine to a uracil comprises incubation of the nucleic acid molecule with bisulfite ion.

5. The method of claim 1, wherein the converting an unmethylated cytosine to a uracil comprises incubation of the nucleic acid molecule with a cytidine deaminase.

6. The method of claim 1, wherein the nucleic acid molecule is DNA.

7. The method of claim 6, wherein the DNA is cell-free DNA (cfDNA).

8. The method of claim 1, wherein the single stranded nucleic acid adapter comprises a universal priming site.

9. The method of claim 1, wherein the single stranded nucleic acid adapter is attached to a solid support.

10. The method of claim 1, wherein the amplifying results in addition of sequencing adapters to the converted nucleic acid molecule or amplification products thereof.

11. The method of claim 1, further comprising determining the methylation profile, wherein the methylation profile is used to screen for or diagnose cancer.

12. The method of claim 1, further comprising determining the methylation profile, wherein the methylation profile is used to determine a tissue or origin of a cell-free DNA.

13. The method of claim 1, wherein the ligase is an RNA ligase.

14. The method of claim 8, wherein the single stranded nucleic acid adapter is ligated to a 3' end of the converted nucleic acid molecule, and the single stranded adapter ligated product comprises the universal priming site.

15. The method of claim 14, wherein the primer of step (d) binds to the universal priming site.

* * * * *